United States Patent [19]

Abichandani et al.

[11] Patent Number: 5,689,025

[45] Date of Patent: *Nov. 18, 1997

[54] ETHYLBENZENE PRODUCTION PROCESS WITH EX SITU SELECTIVATED ZEOLITE CATALYST

[75] Inventors: Jeevan S. Abichandani, Voorhees; Jeffrey S. Beck, Princeton, both of N.J.; Sharon B. McCullen, Newtown, Pa.; David H. Olson, Pennington, N.J.

[73] Assignee: Mobil Oil Corporation, Fairfax, Va.

[*] Notice: The term of this patent shall not extend beyond the expiration date of Pat. No. 5,349,114.

[21] Appl. No.: 382,103

[22] Filed: Feb. 1, 1995

Related U.S. Application Data

[63] Continuation-in-part of Ser. No. 69,251, May 28, 1993, Pat. No. 5,476,823.

[51] Int. Cl.⁶ ............................................. C07C 2/68
[52] U.S. Cl. .................................................. 585/467
[58] Field of Search .............................. 585/475, 481, 585/467

[56] References Cited

U.S. PATENT DOCUMENTS

| | | |
|---|---|---|
| 3,257,310 | 6/1966 | Plank et al. |
| 3,437,587 | 4/1969 | Elbert et al. |
| 3,682,996 | 8/1972 | Kerr |
| 3,698,157 | 10/1972 | Allen et al. |
| 4,016,218 | 4/1977 | Haag et al. |
| 4,060,568 | 11/1977 | Rodewald |
| 4,086,287 | 4/1978 | Kaeding et al. |
| 4,090,981 | 5/1978 | Rodewald |
| 4,100,215 | 7/1978 | Chen |
| 4,107,224 | 8/1978 | Dwyer |
| 4,117,024 | 9/1978 | Kaeding |
| 4,127,616 | 11/1978 | Rodewald |
| 4,145,315 | 3/1979 | Rodewald |
| 4,169,111 | 9/1979 | Wight |
| 4,224,141 | 9/1980 | Morrison et al. |
| 4,283,306 | 8/1981 | Herkes ............................. 585/475 |
| 4,326,994 | 4/1982 | Haag et al. |
| 4,402,867 | 9/1983 | Rodewald |
| 4,443,554 | 4/1984 | Dessau |
| 4,465,886 | 8/1984 | Rodewald |
| 4,477,583 | 10/1984 | Rodewald |
| 4,487,843 | 12/1984 | Telford et al. |
| 4,522,929 | 6/1985 | Chester et al. |
| 4,548,914 | 10/1985 | Chu |
| 4,559,314 | 12/1985 | Shihabi |
| 4,843,057 | 6/1989 | D'Amore et al. |
| 4,851,604 | 7/1989 | Absil et al. |
| 4,927,979 | 5/1990 | Yamagishi et al. |
| 4,950,835 | 8/1990 | Wang et al. |
| 5,157,185 | 10/1992 | Chu et al. |
| 5,173,461 | 12/1992 | Absil et al. |
| 5,321,183 | 6/1994 | Chang et al. ........................ 585/475 |
| 5,349,113 | 9/1994 | Chang et al. ........................ 585/475 |
| 5,349,114 | 9/1994 | Lago et al. ........................... 585/475 |
| 5,365,003 | 11/1994 | Chang et al. ........................ 585/470 |
| 5,367,099 | 11/1994 | Beck et al. .......................... 585/475 |
| 5,382,737 | 1/1995 | Beck et al. .......................... 585/475 |
| 5,403,800 | 4/1995 | Beck et al. ........................... 502/64 |
| 5,406,015 | 4/1995 | Beck et al. .......................... 585/475 |
| 5,455,213 | 10/1995 | Chang et al. ......................... 502/63 |
| 5,475,179 | 12/1995 | Chang et al. ........................ 585/475 |
| 5,476,823 | 12/1995 | Beck et al. ........................... 502/60 |
| 5,488,194 | 1/1996 | Beck et al. .......................... 585/475 |
| 5,495,059 | 2/1996 | Beck et al. .......................... 585/470 |
| 5,498,814 | 3/1996 | Chang et al. ........................ 585/475 |
| 5,516,736 | 5/1996 | Chang et al. ........................ 585/475 |
| 5,516,956 | 5/1996 | Abichandani et al. ................. 585/481 |
| 5,565,004 | 10/1996 | Beck et al. .......................... 585/475 |

FOREIGN PATENT DOCUMENTS 0 296 582 A2  6/1988  European Pat. Off.

OTHER PUBLICATIONS

Nakajima et al., "p–Xylene–Selective Disproportionation of Toluene over a Modified Pentasil Type Zeolite", *Sekiyu Gakkaishi*, 35(2), 185–189 (1992). (no month).

Hibino et al., "Shape–Selectivity over HZSM–5 Modified by Chemical Vapor Deposition of Silicon Alkoxide", *Journal of Catalysis*, 128, 551–558 (1991).

Chen et al., *Shape Selective Catalysis in Industrial Applications*, Marcel Dekker, Inc., New York, pp. 214–217 (1989). (no month).

Lewis et al., "Ethylbenzene Unit Operates Well on Dilute Ethylene," *Oil Gas J.*, 75, 55–58 (1977).

Dwyer et al., "Efficient, Nonpolluting Ethylbenzene Process," *Chem. Eng.*, 83, 90–91 (1976). (no month).

Dwyer, "Mobil/Badger Ethylbenzene Process–Chemistry and Catalytic Implications," in Moser, W.R., ed., *Catalysis of Organic Reactions*, Marcel Dekker, Inc., New York, pp. 39–50 (1981). (no month).

*Primary Examiner*—Steven Bos
*Assistant Examiner*—Thomas G. Dunn, Jr.
*Attorney, Agent, or Firm*—Peter W. Roberts; Dennis P. Santini

[57] ABSTRACT

A process for ethylbenzene production that involves contacting a hydrocarbon feedstream including benzene and ethylene, under alkylation conditions, with a catalytic molecular sieve which has been modified by being ex situ selectivated with a silicon compound. The ex situ selectivation involves exposing the molecular sieve to at least two selectivation sequences, each selectivation sequence comprising contacting the catalyst with a silicon compound followed by calcination. The modified catalyst used in the process may also be steamed. Optionally, the modified catalyst may be trim-selectivated.

21 Claims, No Drawings

ETHYLBENZENE PRODUCTION PROCESS WITH EX SITU SELECTIVATED ZEOLITE CATALYST

CROSS-REFERENCE TO RELATED APPLICATIONS

This is continuation-in-part of application Ser. No. 08/069,251 filed on May 28, 1993 now U.S. Pat. No. 5,476,823. The entire disclosure of the above-cited application is expressly incorporated herein by reference.

BACKGROUND OF THE INVENTION

The present invention is directed to an improved process of alkylation of benzene with ethylene over a modified catalytic molecular sieve.

Ethylbenzene is a valuable commodity chemical which is currently used industrially for the large scale production of styrene monomer. Ethylbenzene may be produced by a number of different chemical processes, but one process which has achieved a significant degree of commercial success is the vapor phase alkylation of benzene with ethylene in the presence of a solid, acidic ZSM-5 zeolite catalyst. In the production of ethylbenzene by this process, ethylene is used as the alkylating agent and is reacted with benzene in the presence of the catalyst at temperatures which vary between the critical temperature of benzene up to 900° F. (about 480° C.) at the reactor inlet. The reactor bed temperature may be as much as 150° F. (about 85° C.) above the reactor inlet temperature and typical temperatures for the benzene/ethylene reaction vary from 600° F. to 900° F. (315° C. to 480° C.), but are usually maintained above about 700° F. (about 371° C.) in order to keep the content of the more highly alkylated benzenes such as diethylbenzene at an acceptably low level. Pressures typically vary from atmospheric to 3000 psig (about 20785 kPa abs) with a molar ratio of benzene to ethylene of from about 1:1 to 25:1, usually about 5:1 (benzene:ethylene). Weight hourly space velocity (WHSV) in the reaction is high, usually in the range of 1 to 6, typically 2 to 5, based on the ethylene flow, with the benzene space velocity varying accordingly, in proportion to the ratio of the reactants. The products of the reaction include ethylbenzene, which is obtained in increasing proportions as temperature increases, together with various polyethylbenzenes, principally diethylbenzene (DIEB), which also are produced in increasing amounts as reaction temperature increases. Under favorable operating conditions on the industrial scale, an ethylene conversion in excess of 90 weight percent (wt. %) may be obtained at the start of the cycle.

In the commercial operation of this process, the polyalkylated benzenes, including both polymethylated and polyethylated benzenes are recycled to the alkylation reactor in which the reaction between the benzene and the ethylene takes place. By recycling the by-products to the alkylation reaction, increased conversion is obtained as the polyethylated benzenes (PEB) are converted to ethylbenzene (EB). In addition, the presence of the PEB during the alkylation reaction reduces formation of these species through equilibration of the components because, at a given feed composition and under specific operating conditions, the PEB recycle will reach equilibrium at a certain level. This commercial process is known as the Mobil/Badger process and is described in more detail in an article by Francis G. Dwyer, entitled "Mobil/Badger Ethylbenzene Process-Chemistry and Catalytic Implications", appearing on pages 39–50 of a book entitled *Catalysis of Organic Reactions*, edited by William R. Moser, Marcel Dekker, Inc. (1981).

Ethylbenzene production processes are described in U.S. Pat. No. 3,751,504 (Keown), U.S. Pat. No. 4,547,605 (Kresge), and U.S. Pat. No. 4,016,218 (Haag); reference is made to these patents for a detailed description of such processes. The process described in U.S. Pat. No. 3,751,504 is of particular note since it includes a separate transalkylation step in the recycle loop which is effective for converting a significant proportion of the more highly alkylated products to the desired ethylbenzene product. Other processes for the production of ethylbenzene are disclosed in U.S. Pat. No. 4,169,111 (Wight) and U.S. Pat. No. 4,459,426 (Inwood), in both of which a preference for large pore size zeolites such as zeolite Y is expressed, in distinction to the intermediate pore size zeolites used in the processes described in the Keown, Kresge and Haag patents. U.S. Pat. No. 3,755,483 (Burress) describes a process for the production of ethylbenzene using zeolite ZSM-12 as the alkylation catalyst.

The term "shape-selective catalysis" describes unexpected catalytic selectivities in zeolites. the principles behind shape selective catalysis have been reviewed extensively, e.g., by Chen et al., *Shape Selective Catalysis in Industrial Applications*, 36, Marcel Dekker, Inc., New York (1989). Within a zeolite pore, hydrocarbon conversion reactions such as paraffin isomerization, olefin skeletal or double bond isomerization, oligomerization and aromatic disproportionation, alkylation or transalkylation reactions are governed by constraints imposed by the channel size.

Several principal shape selectivity constraints operate in zeolite-catalyzed reactions. Reactant selectivity occurs when a fraction of the feedstock is too large to enter the zeolite pores to react. Product selectivity, on the other hand, occurs when some of the products of the reaction cannot leave the zeolite channels. Product distributions can also be altered by transition state selectivity in which certain reactions cannot occur because the reaction transition state is too large to form within the zeolite pores or cages. Another type of selectivity results from configurational constraints on diffusion where the dimensions of the molecule approach that of the zeolite pore system. A small change in the dimensions of the molecule or the zeolite pore can result in large diffusion changes leading to different product distributions. This type of shape selective catalysis is demonstrated, for example, in shape selective alkylations of benzene.

Various methods are known in the art for increasing the selectivity of zeolite catalysts. One such method is to modify the catalyst by treatment with a chemical "selectivating agent". For example, U.S. Pat. Nos. 5,173,461, 4,950,835, 4,927,979, 4,465,886, 4,477,583, 4,379,761, 4,145,315, 4,127,616, 4,100,215, 4,090,981, 4,060,568 and 3,698,157 disclose specific methods for contacting a catalyst with a selectivating agent containing silicon ("silicon-containing selectivating agent"). Other types of selectivating agents are known.

Traditionally, ex situ selectivation of zeolites has involved single applications of the selectivating agent. It may be noted, however, that a suggestion of multiple treatments was made in U.S. Pat. No. 4,283,306 to Herkes. The Herkes patent discloses the promotion of crystalline silica catalyst by application of an amorphous silica such as ethylorthosilicate. The Herkes patent contrasts the performance of catalyst treated once with an ethylorthosilicate solution followed by calcination against the performance of catalyst treated twice with ethylorthosilicate and calcined after each treatment. The Herkes disclosure shows that the twice-treated catalyst is less active and less selective than the once-treated catalyst as measured by methylation of toluene by methanol, indicating that multiple ex situ selectivation confers no benefit and in fact reduces a catalyst's efficacy in shape-selective reactions.

It is well known to alkylate benzene with ethylene by means of zeolite catalysts. Such a process is described in U.S. Pat. No. 4,107,224. The catalyst disclosed in this patent for producing aromatic compounds in high yield is a ZSM-5 type zeolite having 50–75% of the cationic sites occupied by hydrogen ions. Other descriptions of benzene alkylation reactions are given in Dwyer, F. G., and Lewis, P. J., *Chem. Eng.*, 83:90 (1976); Lewis, P. J. and Dwyer, F. G., *Oil Gas J.*, 75:55 (1977); and Chen N. Y., Garwood, W. E., and Dwyer, F. G., *Shape Selective Catalysis in Industrial Applications*, page 214, Marcel Dekker, Inc., New York (1989).

In the vapor phase ethylbenzene (EB) process, the alkylation of benzene with ethylene invariably leads to the formation of a small amount of xylenes (ca. 1000 ppm in the EB product). The xylene isomers exist in thermodynamic equilibrium quantities (i.e., p/m/o:1/2/1). In addition, a substantial portion of the ethylene is consumed in the formation of polyalkylated compounds some of which result in the formation of heavy components (residue) which are rejected. This residue formation is associated with loss of valuable feedstocks, i.e., benzene and ethylene.

The xylenes are undesirable because they cannot be easily separated from the product EB, which is the feed to a styrene unit. Furthermore, from amongst the xylene isomers the ortho-xylene is the most undesirable component, because it is almost impossible to separate it from the styrene, and ends up as an impurity in the finished product.

Therefore, it would be a significant advance in the art to overcome the above-described difficulties, disadvantages and deficiencies associated with conventional benzene alkylation processes in a manner that would enable use of modified catalytic sieves produced by methods which are both more efficient and safer and that would also increase product yields and reduce the proportion of undesirable impurities in the product of such alkylation processes.

The present invention solves the difficulties, disadvantages, and deficiencies inherent in the prior art by providing an improved process for vapor phase alkylation of benzene. The process of the invention produces greater product selectivity, and greater product purity than do conventional processes. The process of the invention also provides substantially reduced levels of undesired by-products, e.g., ortho-xylene and diethylbenzene. In addition, the process of the invention results in substantially lower production of residue, which, in turn, results in substantially greater economy and efficiency of the benzene alkylation process.

Accordingly, it is a purpose of the invention to provide an improved process for the vapor phase alkylation of benzene over a catalytic molecular sieve.

It is a further purpose of the invention to provide an improved process for alkylating benzene which overcomes the above-described difficulties, disadvantages, and deficiencies of the prior art practice of these processes.

Other purposes and advantages of the present invention will be more fully apparent from the following detailed disclosure and appended claims.

SUMMARY OF THE INVENTION

In accordance with the present invention, there is provided a process of vapor phase alkylation of benzene over a modified catalytic molecular sieve by contacting a reaction stream comprising ethylene and benzene, under alkylation conditions, with a modified catalytic molecular sieve. The catalytic molecular sieve found to be useful for the process of the invention has been modified by exposing the catalytic molecular sieve to at least two ex situ selectivation sequences. Each ex situ selectivation sequence includes contacting the catalytic molecular sieve with a silicon-containing selectivating agent, followed by calcination of the contacted catalytic molecular sieve. Selectivating agents useful in the present invention include a large variety of silicon-containing compounds, preferably silicon compounds which are substantially soluble in organic media. Such organic media (i.e., "carriers" for the selectivating agent) include alkanes, preferably paraffins having 3 or more carbons.

In another embodiment, the invention also includes a process of shape selective alkylation of benzene over a modified catalytic molecular sieve that has been further modified by in situ trim-selectivating the modified catalytic molecular sieve. The in situ trim-selectivating may be performed by coke trim-selectivating wherein an organic compound is decomposed in the presence of the modified catalytic molecular sieve, at conditions suitable for decomposing the organic compound. Alternatively, the trim-selectivating may be performed by exposing the modified catalytic molecular sieve to a reaction stream that includes an organic compound and a trim-selectivating agent, including any of a large variety of silicon-containing compounds, at reaction conditions.

Advantageously, the described modified catalysts have enhanced shape selectivity for the alkylation of benzene. Accordingly, the benzene alkylation process of the invention exhibits increased selectivity for ethylbenzene as well as against certain of the by-products of the alkylation process.

For a better understanding of the present invention, together with other and further objects, reference is made to the following detailed description, and its scope will be pointed out in the appended claims.

DETAILED DESCRIPTION OF THE INVENTION

The present invention relates to enhanced shape selective processes for the vapor phase alkylation of benzene with ethylene over modified catalytic molecular sieves.

The catalytic molecular sieves useful according to the invention preferably include intermediate pore zeolites. It is preferred that the catalytic molecular sieves of the invention exhibit a Constraint Index of between about 1 and about 12. The method for determining Constraint Index is described fully in U.S. Pat. No. 4,016,218, incorporated by reference herein. Zeolites which conform to the specified values of Constraint Index for intermediate pore zeolites include ZSM-5, ZSM-11, ZSM-5/ZSM-11 intermediate, ZSM-12, ZSM-22, ZSM-23, ZSM-35, ZSM-48, ZSM-50, and ZSM-57. An especially preferred zeolite is ZSM-5. Such zeolites are described, for example, in U.S. Pat. Nos. 3,702,886 and Re. 29,949, 3,709,979, 3,832,449, 4,046,859, 4,556,447, 4,076,842, 4,016,245, 4,229,424, 4,397,827, 4,640,849, 4,046,685, 3,308,069 and Re. 28,341, to which reference is made for the details of these zeolites.

The catalytic molecular sieves useful for the invention are preferably in the hydrogen, "as-synthesized", form prior to modification, but may be used in the ammonium or sodium form. Other materials may also be present, including hydrogen precursor, organic cations, and combinations thereof.

"Hydrogen precursor" compounds include compounds well known in the art, such as quaternary nitrogen ions, which contain hydrogen substituents and which, upon heating, yield protons. See, for example, U.S. Pat. No. 3,755,483 to Burress, the disclosure of which is incorporated by reference herein.

The crystal size of zeolites used for the invention is preferably greater than about 0.1 micron. The accurate measurement of crystal size of zeolite materials is frequently very difficult. Microscopy methods, such as SEM and TEM, are often used, but these methods require measurements on a large number of crystals, and for each crystal measured, values may be required in up to three dimensions. For ZSM-5 materials described in the examples below, estimates were made of the effective average crystal size by measuring the rate of sorption of 2,2-dimethylbutane at 90° C. and 60 torr hydrocarbon pressure. The crystal size is computed by applying the diffusion equation given by J. Crank, *The Mathematics of Diffusion*, Oxford at the Clarendon Press, 52–56 (1957), for the rate of sorbate uptake by a solid whose diffusion properties can be approximated by a plane sheet model. In addition, the diffusion constant (D) of 2,2-dimethylbutane under these conditions is taken to be $1.5 \times 10^{-14}$ cm$^2$/sec. The relation between crystal size measured in microns, d, the diffusion time measured in minutes, and $t_{0.3}$, the time required for the uptake of 30% of capacity of hydrocarbon, is:

$$d=0.0704 \times t_{0.3}^{1/2}.$$

In the present case, these measurements have been made on a computer controlled, thermogravimetric electrobalance, but there are numerous ways by which one skilled in the art could obtain such data. The crystal material preferred for the invention has a sorption time, $t_{0.3}$, of 7.8 minutes, and a calculated crystal size of 0.20 micron.

The "alpha value" of a catalyst is an approximate indication of the catalytic cracking activity of the catalyst compared to a standard catalyst, and it gives the relative rate constant (rate of normal hexane conversion per volume of catalyst per unit time). It is based on the activity of the amorphous silica-alumina cracking catalyst taken as an alpha of 1 (Rate Constant=0.16 sec$^{-1}$). The alpha test is described in U.S. Pat. No. 3,354,078 and in *Journal of Catalysis*, 4, 522–529 (1965); 6, 278 (1966); 61, 395 (1980), each incorporated herein by reference as to that description. It is noted that intrinsic rate constants for many acid-catalyzed reactions are proportional to the alpha value for a particular crystalline silicate catalyst (see "The Active Site of Acidic Aluminosilicate Catalysts", *Nature*, 309, 589–591 (14 Jun. 1984). The experimental conditions of the test used herein include a constant temperature of 538° C. and a variable flow rate as described in detail in the *Journal of Catalysis*, 61, 395 (1980). The alkylation process of the present invention generally requires a catalyst having acidic activity. Such catalysts generally have an alpha value greater than 1, for example, from about 1 to about 2000, preferably from about 10 to about 500, more preferably from about 10 to about 100. The alpha value of the catalyst may be increased by initially treating the catalyst by mild steaming. This type of steaming is discussed in U.S. Pat. No. 4,326, 994.

The silica to alumina ratio (SiO$_2$/Al$_2$O$_3$) of the catalysts of the invention may be determined by conventional analysis. This ratio is meant to represent, as closely as possible, the ratio in the rigid atomic framework of the zeolite crystal and to exclude aluminum in the binder or in cationic or other form within the channels. Although zeolites with a silica to alumina ratio of up to about 200 are useful, it is preferred to use zeolites having ratios of at least about 20 to about 1000.

For the improved benzene alkylation processes of this invention, the suitable molecular sieve may be employed in combination with a support or binder material such as, for example, a porous inorganic oxide support or a clay binder. While the preferred binder is silica, other non-acidic binder materials may be employed, generally in the form of dried inorganic oxide gels or gelatinous precipitates. Suitable clay materials include, by way of example, bentonite and kieselguhr. The relative proportion of suitable crystalline molecular sieve to the total composition of catalyst and binder or support may be from about 5% to about 98% by weight and is preferably from about 25% to about 80% by weight of the composition. The composition may be in the form of an extrudate, beads or fluidizable microspheres. The catalyst may also be used in self-bound form.

In conventional applications, the silicon compound employed may be in the form of a solution, an emulsion, or a gas under the conditions of contact with a zeolite. For the modification of catalysts according to the invention, the silicon compound is preferably contacted with the catalyst as a liquid, most preferably a solution including a silicon-containing selectivating agent dissolved in an organic carrier. The deposited silicon compound preferably extensively covers, and resides substantially exclusively on, the external surface of the molecular sieve. Examples of methods of depositing silicon on the surface of the zeolite are found in U.S. Pat. Nos. 4,090,981, 4,127,616, 4,465,886 and 4,477, 583, which are incorporated by reference herein. Other examples of the deposition of a silicon compound on zeolite surfaces are described in Nakajima et al., *Sekiyu Gakkaishi*, 35, 185–189 (1992), and in U.S. Pat. No. 4,950,835.

For the modification method of the present invention, a zeolite, either incorporated with a binder or in unbound form, is contacted at least twice, preferably between about two and about six times, with a selectivating agent dissolved in an organic solvent. The selectivating agent comprises a compound or polymer containing a main group or transition metal, preferably silicon. The catalyst is contacted with a solution of the silicon-containing selectivating agent in an organic solvent at a catalyst/selectivating agent weight ratio of from about 100/1 to about 1/10, at a temperature of from about 10° C. to about 150° C., at a pressure of from about 0 psig to about 200 psig, for a time of from about 0.1 hr to about 24 hours. The organic carrier is preferably removed, e.g., by distillation or evaporation, with or without vacuum. The catalyst is then calcined. This methodological sequence comprising the step of contacting of the catalyst with the selectivating agent solution and the step of calcining the contacted catalyst is termed a "selectivation sequence." The catalysts of the invention, then, are exposed to at least two of these selectivation sequences.

As used herein, the term "selectivating agent" is used to indicate substances which will increase the shape-selectivity of a catalytic molecular sieve to the-desired levels while maintaining commercially acceptable levels of hydrocarbon conversion. Such substances include, for example, organic silicon compounds such as phenylmethyl silicone, dimethyl silicone, and blends thereof which have been found to be suitable. In general, such organosilicon compounds must be soluble in organic solvents such as those described elsewhere herein. In addition, a "solution" is intended to mean a uniformly dispersed mixture of one or mores substances at a molecular or ionic level. The skilled artisan will appreciate that solutions, both ideal and colloidal, differ from emulsions.

Useful selectivating agents include silicones and silicone polymers which can be characterized by the general formula:

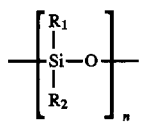

where $R_1$ is hydrogen, halogen, hydroxyl, alkyl, halogenated alkyl, aryl, halogenated aryl, aralkyl, halogenated aralkyl, alkaryl or halogenated alkaryl. The hydrocarbon substituents generally contain from 1 to 10 carbon atoms, preferably methyl or ethyl groups. $R_2$ is independently selected from the same group as $R_1$, and n is an integer of at least 2 and generally in the range of 3 to 1000. The molecular weight of the silicone compound employed is generally between about 80 and about 20,000 and preferably within the approximate range of 150 to 10,000. Representative silicone compounds include dimethyl silicone, diethyl silicone, phenylmethyl silicone, methylhydrogen silicone, ethylhydrogen silicone, phenylhydrogen silicone, methylethyl silicone, phenylethyl silicone, diphenyl silicone, methyltrifluoropropyl silicone, ethyltrifluoropropyl silicone, polydimethyl silicone, tetrachlorophenylmethyl silicone, tetrachlorophenylethyl silicone, tetrachlorophenylhydrogen silicone, tetrachlorophenylphenyl silicone, methylvinyl silicone and ethylvinyl silicone. The silicone compound need not be linear, but may be cyclic, for example, hexamethyl cyclotrisiloxane, octamethyl cyclotetrasiloxane, hexaphenyl cyclotrisiloxane and octaphenyl cyclotetrasiloxane. Mixtures of these compounds may also be used, as may silicones with other functional groups.

Other silicon compounds, including silanes and alkoxy silanes, such as tetramethoxy silane, may also be utilized. These useful silicon-containing selectivating agents include silanes and alkoxysilanes characterizable by the general formula:

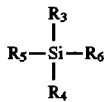

where $R_1$, $R_2$, $R_3$ and $R_4$ are independently selected from the group consisting of hydrogen, hydroxyl, halogen, alkyl, halogenated alkyl, alkoxy, aryl, halogenated aryl, aralkyl, halogenated aralkyl, alkaryl, and halogenated alkaryl groups. Mixtures of these compounds may also be used.

Preferred silicon-containing selectivating agents include dimethylphenylmethyl polysiloxane (e.g., Dow-550) and phenylmethyl polysilocane (e.g., Dow-710). Dow-550 and Dow-710 are available from Dow Chemical Co., Midland, Mich.

Preferably, the kinetic diameter of the high efficiency, selectivating agent is larger than the zeolite pore diameter, in order to avoid entry of the selectivating agent into the pore and any concomitant reduction in the internal activity of the catalyst.

Examples of suitable organic media (carriers) for the organosilicon selectivating agent include linear, branched, and cyclic alkanes having three or more carbons. In the methods of the present invention it is preferred that the carrier is a linear, branched, or cyclic alkane having a boiling point greater than about 70° C., and preferably containing 7 or more carbons. Optionally, mixtures of low volatility organic compounds, such as hydrocracker recycle oil, may be employed as carriers. Especially preferred low volatility hydrocarbon carriers of selectivating agents include decane and dodecane.

It has been found that a scheme comprising at least two selectivation sequences provides increased efficiency of deposition of the silicon compound on the surface of the catalyst. This increased efficiency allows for the use of relatively small quantities of the silicon compound as well as relatively small quantities of the solvent carrier. Accordingly, the amount of silica deposited on the catalyst, as a fraction of the silicon compound in the selectivating agent solution, tends to be greater when the deposition is performed stepwise in a sequential fashion according to the invention, than when the deposition is made entirely by a single contacting of the catalyst with the selectivating agent. In addition, it has been observed that the activity and selectivity of the catalysts modified by multiple selectivation sequences tend to be substantially higher than the activity and selectivity of a catalyst modified by the deposition of a comparable amount of silica in a single step.

Following each contacting of the catalyst with a silicon compound, wherein the silicon compound is deposited, the contacted catalyst is calcined to decompose the molecular or polymeric species to a solid state species. The catalyst may be calcined by increasing the temperature at a rate of from about 0.2° C./minute to about 5° C./minute, until reaching a temperature greater than 200° C., but below a temperature at which the crystallinity of the zeolite is adversely affected. Generally, such temperature will be below 600° C. Preferably the temperature of calcination is within the approximate range of 350° C. to 550° C. The product is maintained at the calcination temperature usually for 1 to 24 hours, preferably for between 2 and 6 hours.

The calcination process may be performed in an atmosphere of $N_2$, an oxygen-containing atmosphere, preferably air, an atmosphere of $N_2$ followed by an oxygen-containing atmosphere, or an atmosphere containing a mixture of $N_2$ and air. Calcination should be performed in an atmosphere substantially free of water vapor, to avoid undesirable uncontrolled steaming of the catalyst. The catalyst may be calcined once or more than once after each contacting with a selectivating agent. The various calcinations in any selectivation sequence need not be identical, but may vary with respect to the temperature, the rate of temperature rise, the atmosphere and the duration of calcination.

Factors upon which the amount of silica incorporated with the zeolite is dependent include temperature of contact with the selectivating agent, the type and concentration of the silicon compound in the contacting medium, the degree to which the zeolite has been dried prior to contact with the silicon compound, the conditions of calcination of the contacted zeolite, and the number of selectivation sequences performed.

Subsequent to the ex situ selectivation of the catalyst, the catalyst may be further modified in situ, i.e., in the reactor in which the process of hydrocarbon conversion is performed.

The feed of benzene and ethylene may be co-fed simultaneously with a second selectivating agent and hydrogen at reaction conditions until the desired ethylbenzene selectivity, e.g., 90%, is attained, whereupon the co-feed of selectivating agent is discontinued. This co-feeding of selectivating agent is discontinued. This co-feeding of selectivating agent with the hydrocarbon feed is a type of "trim-selectivation" or "in situ selectivation". Reaction conditions for this in situ selectivation step generally include a temperature of from about 350° C. to about 540° C., and a pressure of from about atmospheric to about 5000 psig. The reaction stream is fed to the system at a rate of from about 0.1 WHSV to about 20 WHSV. Hydrogen may be fed at a hydrogen to hydrocarbon molar ratio of from about 0.1 to about 20.

The selectivating agent for trim-selectivation may be selected from among the exemplary silicon compounds discussed in greater detail above with respect to ex situ selectivation. For example, organic silicon compounds such as phenylmethyl silicone, dimethyl silicone, and mixtures thereof are suitable. According to one embodiment of the present invention, a silicone containing phenylmethyl-silicone and dimethylsilicone groups in a ratio of about 1:1 is co-fed to the system, while the other components, e.g., hydrocarbon and hydrogen, are fed in the amounts set forth above. The selectivating agent is co-fed in an amount of from about 0.001 wt % to about 10 wt. % of the hydrocarbon according to this preferred embodiment. Depending upon the percentage of selectivating agent used, the trimselectivation will last for at least one hour, preferably about 1 to about 48 hours, more preferably less than 24 hours.

In this scheme the silicon compound will decompose to deposit additional silica to on the catalyst. During the in situ selectivation procedure the selectivity of the catalyst will be observed to increase further. The silicon-containing polymer or molecular species may be dissolved in toluene or other appropriate aromatic or hydrocarbon carrier.

Alternatively, the catalyst, prior to contacting with hydrocarbon under alkylation conditions, may be subjected to a trim-selectivation process known as "coke trimming". This process involves exposing the modified catalyst to a thermally decomposable organic compound at an elevated temperature in excess of the decomposition temperature of said compound but below the temperature at which crystallinity of the zeolite is adversely affected. Generally, this temperature will be less than about 650° C.

Organic materials, thermally decomposable under the above temperature conditions to provide coke trimming, encompass a wide variety of compounds including by way of example, hydrocarbons, such as paraffinic, cycloparaffinic, olefinic, cycloolefinic and aromatic; oxygen-containing organic compounds such as alcohols, aldehydes, ethers, ketones and phenols; heterocyclics such as furans, thiophenes, pyrroles and pyridines. Usually, it is contemplated that a thermally decomposable hydrocarbon, such as an olefin or paraffin, will be the source of coke, most preferably the ethylene itself being subjected to benzene alkylation. In the latter case, the hydrocarbon is initially brought into contact with the catalyst under conditions of temperature and hydrogen concentration amenable to rapid coke formation. Typically, coke trimming is conducted at conditions outside the operating parameters used during the main time span of the catalytic cycle. When the desired coke deposition has been effected, the hydrocarbon feed is continued in contact with the coke-containing catalyst under conditions of temperature and hydrogen concentration conducive to benzene alkylation, with a greatly reduced coking rate.

Alkylation of Benzene

The modified zeolite catalysts useful in the present invention are advantageously used in the alkylation of benzene with ethylene to provide ethylbenzene (EB). Alkylations of benzene in which the catalysts of the invention can be used are described, for example, in U.S. Pat. No. 4,107,224, the disclosure of which is incorporated herein by reference.

The alkylation reaction is carried out at elevated temperatures in the vapor phase. Suitable conditions can be selected by reference to the phase diagram for benzene. In the vapor phase reaction, the conditions are selected to maintain the benzene in the vapor phase, for example, with a reactor inlet temperature which is above the temperature required to maintain the benzene in the vapor phase at the selected pressure, with a preferred maximum of about 900° F. (about 480° C.). Because the reaction is exothermic, the reactor bed temperature will be higher than the reactor inlet temperatures, typically by as much as about 150° F. (about 85° C.), but generally it is preferred to control the exotherm to a maximum of about 100° F. (about 55° C.). In most cases, the reaction temperature will be from about 300° F. (about 150° C.) to about 850° F. (about 455° C.) with a yield of ethylbenzene increasing with increasing temperatures. Normally, a temperature of at least 500° F. (about 260° C.) will be used. Because the yield of PEB and certain other by-products usually decreases with increasing temperature, higher temperatures toward 900° F. (about 480° C.) would be preferred, although a disadvantage of these higher temperatures is that the yield of xylenes would be increased. The weight ratio of ethylbenzene to diethylbenzene produced in the vapor phase alkylation step may be from about 2 to about 30.

Pressures during the vapor phase alkylation step typically are between atmospheric and about 3000 psig (about 20785 kPa abs) and generally will not exceed 1000 psig (about 7000 kPa abs). Relatively low temperature atmospheric pressures, for example, about 50 or 100 psig (about 445 or 790 kPa abs), sufficient to maintain the desired flow rates through the reaction bed, will normally be satisfactory. The reaction is preferably carried out in the absence of hydrogen and, accordingly, the prevailing pressures are usually those of the reactant species. In a typical low pressure vapor phase operation, the temperature will be from about 600° F. to about 800° F., (315° C. to 427° C.), with the pressure from about 50 psig to about 500 psig, usually from about 200 psig to about 500 psig.

The space velocity may be from about 0.1 to about 10 WHSV, based on the ethylene feed, but is usually maintained at a relatively high value, e.g., from about 1 to about 10 WHSV, typically between about 1 and about 6 WHSV, based on the ethylene, for the gas phase reaction.

The ratio of the benzene to the ethylene in the alkylation reactor is typically about 1:1 on a molar basis (benzene:ethylene, fresh feed). The ratio in the reactors may be higher as a result of the benzene recycle, with ratios above 20:1 being possible, typically about 5:1 to about 30:1.

The use of temperatures significantly above about 950° F. is undesirable because, at these high temperatures, various undesirable reactions occur. The reactants and the alkylated products undergo degradation resulting in the loss of the desired products as well as the reactants. In addition, undesirable residues may be formed from other side reactions. The ethylene which functions as the alkylating agent will tend to polymerize with itself, especially at high pressures or with other reactants, forming resinous compounds within the reaction zone. These resinous compounds together with the degradation products may lead to the formation of coke-like deposits on the active surfaces of the catalyst which will rapidly inhibit the high activity necessary in the catalyst for acceptable conversion rates. The use of temperatures below about 900° F. (about 480° C.) will normally enable these problems to be maintained within acceptable bounds.

The alkylation process can be carried out as a batch-type, semi-continuous or continuous operation utilizing a fixed, fluidized or moving bed catalyst system. The process is, however, preferably operated in the general manner described in U.S. Pat. No. 3,751,504 (Keown). Reference is made to U.S. Pat. No. 3,751,504 for a description of the process configuration. The use of a separate vapor phase transalkylation reactor in the recycle loop for the higher alkylated products is described in the Keown patent.

It will be understood that the hydrocarbon feed to the transalkylation step may comprise other hydrocarbons in addition to benzene and diethylbenzenes. These hydrocarbons include byproducts from the vapor phase alkylation step which are carried over along with diethylbenzenes when diethylbenzenes are removed from the ethylbenzene product from the vapor phase alkylation step. These other hydrocarbons may include cumene, butylbenzenes and other polyethylbenzenes, such as triethylbenzenes. To the extent that other polyethylbenzenes, such as triethylbenzenes, are included in the feed to the transalkylation step, these other polyalkylbenzenes can contribute to the yield of ethylbenzene products obtained via transalkylation reactions of the polyethylbenzenes with benzene.

As used herein, the term "ethylbenzene selectivity" means the proportion of ethylbenzene, indicated as a percentage, among all of the products of the alkylation reaction.

The present invention is described in detail below in relation to the alkylation of benzene over a multiply-selectivated catalyst. Normally a single pass conversion of a hydrocarbon stream, comprising benzene and ethylene, results in a product stream which includes ethylbenzene along with various $C_6$–$C_8$ aromatics such as benzene, toluene, mixed xylenes and other $C_8$ aromatics as well as a variety of $C_{9+}$ aromatics and polyalkylated aromatics. The product stream produced by conventional benzene alkylation processes generally carries an unacceptably high $C_{9+}$ polyalkylated aromatics content.

In the vapor phase ethylbenzene (EB) process, the alkylation of benzene with ethylene invariably leads to the formation of a small amount of xylenes (ca. 1000 ppm in the EB product). The xylene isomers exist in thermodynamic equilibrium quantities (i.e. p/m/o:1/2/1). In addition, a substantial portion of the ethylene is consumed in the formation of polyalkylated compounds some of which result in the formation of heavy components (residue) which are rejected. This residue formation is associated with loss of valuable feedstocks, benzene and ethylene.

The xylenes are undesirable because they cannot be easily separated from the product EB, which is the feed to a styrene unit. Furthermore, from amongst the xylene isomers the ortho-xylene is the most undesirable component, because it is almost impossible to separate from the styrene, and ends up as an impurity in the finished product.

Typically, the polyalkylated compounds are isolated and either recycled back to the reactor or to a separate transalkylator. The major component in the polyalkylated benzenes is diethylbenzene (DEB). The primary function of the transalkylator is to transalkylate DEB with benzene to produce more EB. However, the other polyalkylated compounds, such as n-propyl benzene and n-butyl benzene can only be removed by dealkylation. Therefore, in reality the transalkylator is also a dealkylator, and hence its catalyst selection and operating conditions are a compromise between the optimum for transalkylation and dealkylation. Due to this compromise some of the products of dealkylation react further with polyalkylated compounds to form more residue. In contrast, a catalyst treated in the manner described herein yields a significantly ethylbenzene-enriched product from benzene alkylation with ethylene.

The properties of the catalyst of the invention also greatly reduce ortho-xylene make, shifting the isomer concentrations of the xylenes substantially away from thermodynamic equilibrium. The shape selective properties of the catalyst described herein also inhibit the formation of larger polyalkylated molecules. This reduces the residue make, which, in turn, increases the utilization of ethylene and benzene towards formation of more desirable products. Additionally, the constraints of the catalyst useful for the invention affect the production of diethylbenzene isomers, generally allowing the escape from the catalyst of only the para-diethylbenzene isomer. Therefore, almost pure para-DEB may be taken as a by-product, leaving all other polyalkylated materials to be diverted to a dealkylation unit. Since this secondary reactor is then a true dealkylation unit, it does not require any compromise in catalyst selection on operating conditions, enhancing the utility of the process by further limiting residue formation.

As explained in greater detail elsewhere herein, the present invention provides a process for obtaining ethylene conversions of at least about 95%, preferably at least about 98%, with an ethylbenzene selectivity of greater than about 90%, preferably at least about 95%.

The hydrocarbon feed may also contain diluents. Diluents may include other hydrocarbons such as methane and ethane, which may be present in the feed in aggregate amounts greater than the quantity of ethylene of benzene. Other diluents include gases such as hydrogen, nitrogen, carbon monoxide, carbon dioxide and mixtures thereof.

The feed stream may also include various impurities such as water, hydrogen sulfide and other organic compounds in small amounts, provided that the purity of the product is not greatly compromised.

The hydrocarbon feedstock may also be dried, if desired, in a manner which will minimize moisture entering the reaction zone. Numerous methods known in the art are suitable for drying the hydrocarbon charge for the process of the invention. These methods include percolation through any suitable desiccant, for example, silica gel, activated alumina, molecular sieves or other suitable substances, or the use of liquid charge dryers.

Operating conditions employed in the process of the present invention will affect the ethylbenzene selectivity and hydrocarbon conversion. Such conditions include the temperature, pressure, space velocity, molar ratio of the reactants, and the hydrogen to hydrocarbon mole ratio ($H_2$/HC). It has also been observed that an increased space velocity (WHSV) can enhance the selectivity of the modified catalyst in benzene alkylation reactions. This characteristic of the modified catalyst allows for substantially improved throughput when compared to current commercial practices. In addition, it has been observed that the alkylation process may be performed using $H_2$ as a diluent, thereby dramatically increasing the cycle length of the catalyst. For example, it has been observed that an increase in temperature can increase the activity of the modified catalyst.

The following Examples further illustrate the various features of the invention, and are not intended in any way to limit the scope of the invention, which is defined in the appended claims.

EXAMPLE 1

In a first ex situ selectivation sequence, 100 grams of dry silica-bound HZSM-5 having a crystal size of 0.2 micron was contacted with 102 grams of a 7.3% solution of dimethylphenylmethyl polysilicone (Dow-550) in dodecane at room temperature with mixing for two hours. The sample was filtered and then calcined. The moist sample was heated in 400 cc/min $N_2$ at a heating rate of 1° C./min to 140° C. and held for two hours. After two hours at 140° C., the sample was heated at 2° C./min to 540° C. and held for two hours. The sample was then cooled to 300° C. in nitrogen at which time air was introduced followed by heating in air at 2° C./min to 540° C. and held for 6 hours. The weight uptake was 3.0% $SiO_2$.

In a second ex situ selectivation sequence, all of the once-treated catalyst was contacted with 105 grams of a 7.3% Dow 550/dodecane solution at room temperature with mixing for two hours. The sample was filtered and then calcined as described above for the first selectivation sequence. The weight uptake was 2.65% $SiO_2$.

In a third ex situ selectivation sequence, 98 grams of the twice-treated catalyst was contacted with 98 grams of 7.3% Dow 550/dodecane solution at room temperature with mixing for two hours. The sample was filtered and then calcined as described above for the first selectivation sequence. The weight uptake was 2.65% $SiO_2$.

In a fourth ex situ selectivation sequence, 40 grams of the three-times treated catalyst was contacted with 40 grams of a 7.3% Dow 550/dodecane solution at room temperature with mixing for two hours. The sample was filtered and then calcined as described above for the first selectivation sequence. The weight uptake was 2.45% $SiO_2$.

In a fifth ex situ selectivation sequence, 42 grams of the four-times treated catalyst was contacted with 42 grams of a 5.2% Dow 550/dodecane solution at room temperature with mixing for two hours. The sample was filtered and then calcined as described above for the first selectivation sequence. The weight uptake was 1.3% $SiO_2$. The total silica weight uptake for the 5-step ex situ selectivation process was about 10%.

EXAMPLE 2

The five-times selectivated catalyst of Example 1 was employed for the disproportionation of toluene under conditions comprising a toluene WHSV of 3 $hr^{-1}$, a $H_2/HC$ molar ratio of 1, a pressure of 300 psig, and a temperature of 760° F. to 800° F.

Data obtained from this reaction are illustrated in FIG. 1. At toluene conversion rates of from 28.7% to 36.1%, the para-xylene selectivity was at least 92.4% to 87.8%. Within the xylenes fraction, no more than 1% of meta-xylene was produced. Moreover, no more than 500 ppm of o-xylene was produced. (For a non-shape selective catalyst, the expected xylene distribution would be 24% para-, 50% meta-, and 26% ortho-xylene) This extremely low ortho-xylene make indicates that in the ethylation of benzene, the generation of ortho-xylene would be substantially reduced as compared to conventional processes. Accordingly, because of the difficulty of removing ortho-xylene from ethylbenzene, the purity of the product of an ethylbenzene production process using this catalyst would be expected to be substantially higher than the product of ethylbenzene production processes using conventional catalysts.

EXAMPLE 3

The five-times selectivated catalyst of Example 1 is employed for the alkylation of benzene with ethylene under conditions comprising an ethylene WHSV of from 2 to 4 $hr^{-1}$, a benzene to ethylene weight ratio of 20, a pressure of 250 psig, and a temperature of 750° F.

The ethylene conversion is greater than 95% in a single pass. The ethylbenzene purity is greater than 95%. No more than 5% of $C_{9+}$ is produced (reduced residue make), along with no more than 500 ppm of p-xylene. Moreover, no more than 20 ppm of o-xylene is produced. Almost pure (>75%) para-diethylbenzene (para-DEB) is taken as a transalkylation by-product. Para-DEB, uncontaminated with meta and ortho isomers, is a very valuable commodity and commands a high price.

While the invention has been described with reference to specific embodiments, it will be apparent that numerous variations, modifications, and alternative embodiments of the invention are possible, and accordingly all such variations, modifications, and alternative embodiments are to be regarded as being within the spirit and scope of the present invention as claimed.

What is claimed is:

1. A process for improved shape selective alkylation of benzene comprising:

contacting a reaction stream comprising ethylene and benzene, under alkylation conditions sufficient to produce ethylbenzene, with a catalytic molecular sieve which comprises a zeolite having a constraint index of from about 1 to about 12 and which has been modified by being exposed to at least two ex-situ selectivation sequences;

wherein each ex-situ selectivation sequence includes the steps of contacting the catalytic molecular sieve with a selectivating agent dissolved in an organic carrier and subsequently calcining the catalytic molecular sieve.

2. A process of claim 1, wherein the alkylation conditions comprise a temperature of from about 150° C. to about 480° C., a pressure of from about 0.1 atmosphere to about 200 atmospheres, and a weight hourly space velocity of from about 0.1 to about 10.

3. The process of claim 2, wherein the alkylation conditions further comprise a hydrogen/hydrocarbon mole ratio of from greater than 0 to about 100.

4. The process of claim 1, wherein the catalytic molecular sieve has been modified by between two and six ex situ selectivation sequences.

5. The process of claim 1, wherein the selectivating agent comprises a silicon compound selected from the group consisting of

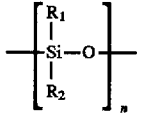

wherein $R_1$ and $R_2$ are independently selected from the group consisting of hydrogen, halogen, hydroxyl, alkyl, alkoxy, halogenated alkyl, aryl, halogenated aryl, aralkyl, halogenated aralkyl, alkaryl, and halogenated alkaryl, and n is between 2 and 1000; and

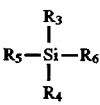

wherein $R_3$, $R_4$, $R_5$ and $R_6$ are independently selected from the group consisting of hydrogen, halogen, hydroxyl, alkyl, alkoxy, halogenated alkyl, aryl, halogenated aryl, aralkyl, halogenated aralkyl, alkaryl, and halogenated alkaryl.

6. The process of claim 5, wherein the selectivating agent comprises dimethylphenylmethyl polysiloxane.

7. The process of claim 1, wherein the organic carrier comprises a linear, branched, or cyclic hydrocarbon.

8. The process of claim 7, wherein the organic carrier is a paraffin containing at least 7 carbon atoms.

9. The process of claim 8, wherein the organic carrier comprises dodecane.

10. The process of claim 7, wherein the organic carrier component comprises hydrocracker recycle oil.

11. The process of claim 1, wherein the catalytic molecular sieve contains an ion selected from the group consisting of hydrogen, hydrogen precursor, organic cations, and combinations thereof.

12. The process of claim 11, wherein the catalytic molecular sieve is modified in an as-synthesized condition.

13. The process of claim 1, wherein the modified catalytic molecular sieve has been further modified by the step of steaming the modified catalytic molecular sieve.

14. The process of claim 1, wherein the modified catalytic molecular sieve has been further modified by the step of in situ trim-selectivating the modified catalytic molecular sieve.

15. The process of claim 14, wherein the in situ trim-selectivating step comprises contacting the modified catalytic molecular sieve with a thermally decomposable organic compound selected from the group consisting of paraffins, cycloparaffins, olefins, cycloolefins, aromatics, alcohols, aldehydes, ethers, ketones, phenols, heterocyclics, and mixtures thereof, at a temperature in excess of the decomposition temperature of the thermally decomposable organic compound.

16. The process of claim 15, wherein the thermally decomposable organic compound is ethylene.

17. The process of claim 15, wherein the in situ trim-selectivating step comprises contacting the modified catalytic molecular sieve with a reaction stream comprising hydrocarbon and a trim-selectivating agent.

18. The process of claim 1, further comprising the step of transalkylating polyethylbenzenes produced during said contacting step.

19. The process of claim 18, wherein said transalkylating step comprises recycling said polyethylbenzenes into said reaction stream.

20. The process of claim 18, wherein said transalkylating step comprises introducing said polyethylbenzenes into a separate transalkylation reactor and reacting said polyethylbenzenes with benzene under sufficient vapor phase or liquid phase conditions to produce ethylbenzene.

21. The process of claim 20, further comprising the step of combining said ethylbenzene produced during said transalkylating step with said ethylbenzene produced in said contacting step.

* * * * *